United States Patent
Wagstaff

(10) Patent No.: US 6,792,642 B2
(45) Date of Patent: Sep. 21, 2004

(54) TONGUE CLEANING DEVICE

(75) Inventor: Robert K. Wagstaff, Bountiful, UT (US)

(73) Assignee: Dr. Bob's Ltd., Bountiful, UT (US)

( * ) Notice: Subject to any disclaimer, the term of this patent is extended or adjusted under 35 U.S.C. 154(b) by 309 days.

(21) Appl. No.: 10/027,480

(22) Filed: Dec. 21, 2001

(65) Prior Publication Data

US 2003/0115699 A1 Jun. 26, 2003

(51) Int. Cl.[7] .............................. A46B 9/02; A46B 9/06; A61B 17/24

(52) U.S. Cl. .................. 15/160; 15/111; 15/167.1; 606/161

(58) Field of Search .................. 15/111, 160, 167.1, 15/207.2, 187, DIG. 5; 606/160, 161, 162, 167

(56) References Cited

U.S. PATENT DOCUMENTS

| | | | |
|---|---|---|---|
| 2,637,870 A | * | 5/1953 | Cohen ........................ 433/141 |
| 5,282,814 A | | 2/1994 | Srivastava |
| 5,613,262 A | | 3/1997 | Choy-Maldonado |
| 5,735,864 A | | 4/1998 | Heisinger, Jr. |
| 5,766,193 A | | 6/1998 | Millner |
| 5,842,247 A | | 12/1998 | Decesare |
| 5,881,422 A | | 3/1999 | Narwani |
| 5,916,228 A | | 6/1999 | Ripich et al. |
| 6,015,293 A | * | 1/2000 | Rimkus ........................ 433/141 |
| 6,032,315 A | * | 3/2000 | Liebel .......................... 15/160 |
| 6,102,923 A | * | 8/2000 | Murayama .................. 606/161 |
| 6,131,228 A | | 10/2000 | Chen et al. |
| 6,171,323 B1 | | 1/2001 | Potti et al. |
| 6,352,545 B1 | * | 3/2002 | Wagner ....................... 606/161 |

* cited by examiner

Primary Examiner—Robert J. Warden, Sr.
Assistant Examiner—S Balsis
(74) Attorney, Agent, or Firm—Daniel P. McCarthy; Parsons Behle & Latimer

(57) ABSTRACT

Devices for cleaning the human tongue and methods for making such devices are disclosed. The tongue cleaner may include a tongue brush and a tongue scraper. The tongue cleaner may be of unitary injection molded construction. The tongue cleaner bristles may be tapered to a point for cleaning crevices of a human tongue, and the bristles may be angled or curved. The tongue scraper contains at least one blade for removal of undesirable material from the tongue by a scraping action. The tongue brush and tongue scraper may be combined into one unit or may be made and used separately.

25 Claims, 10 Drawing Sheets

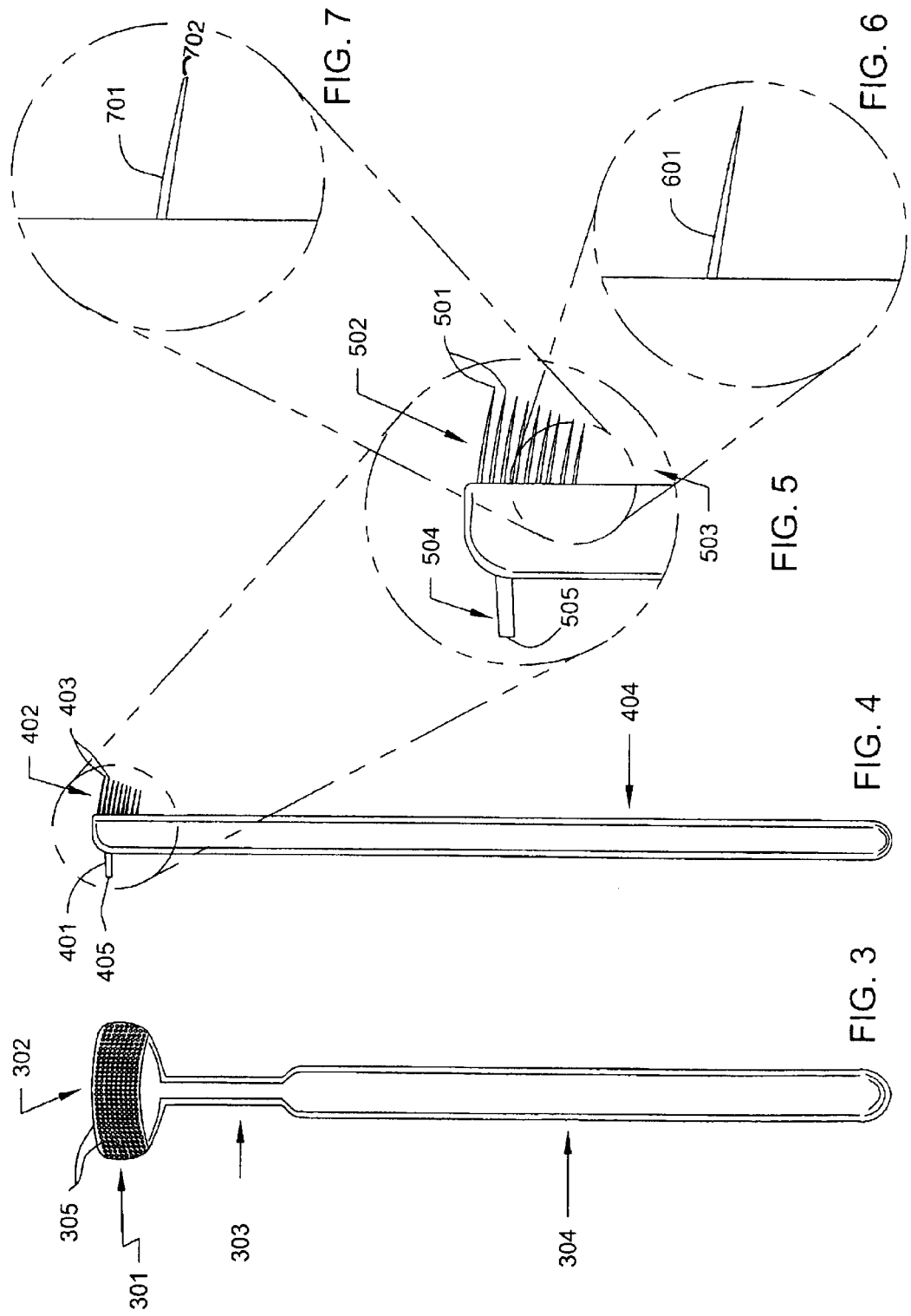

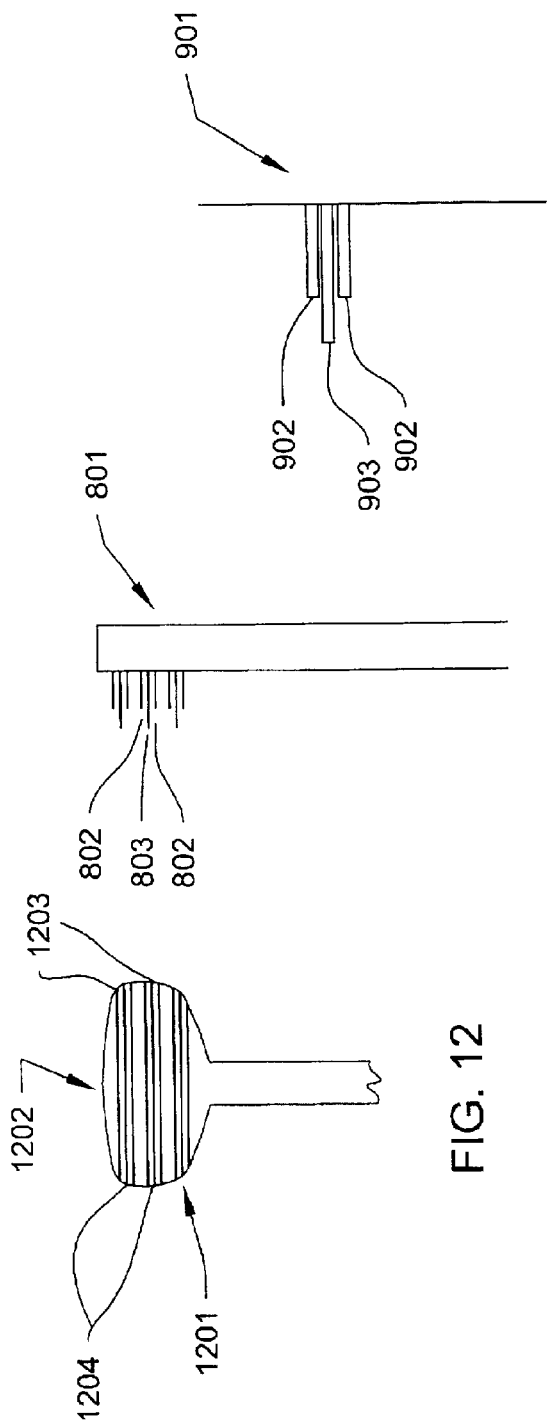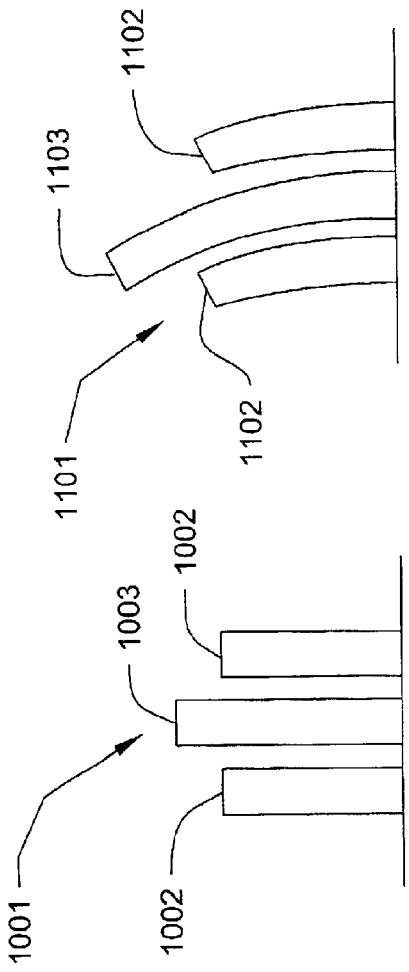

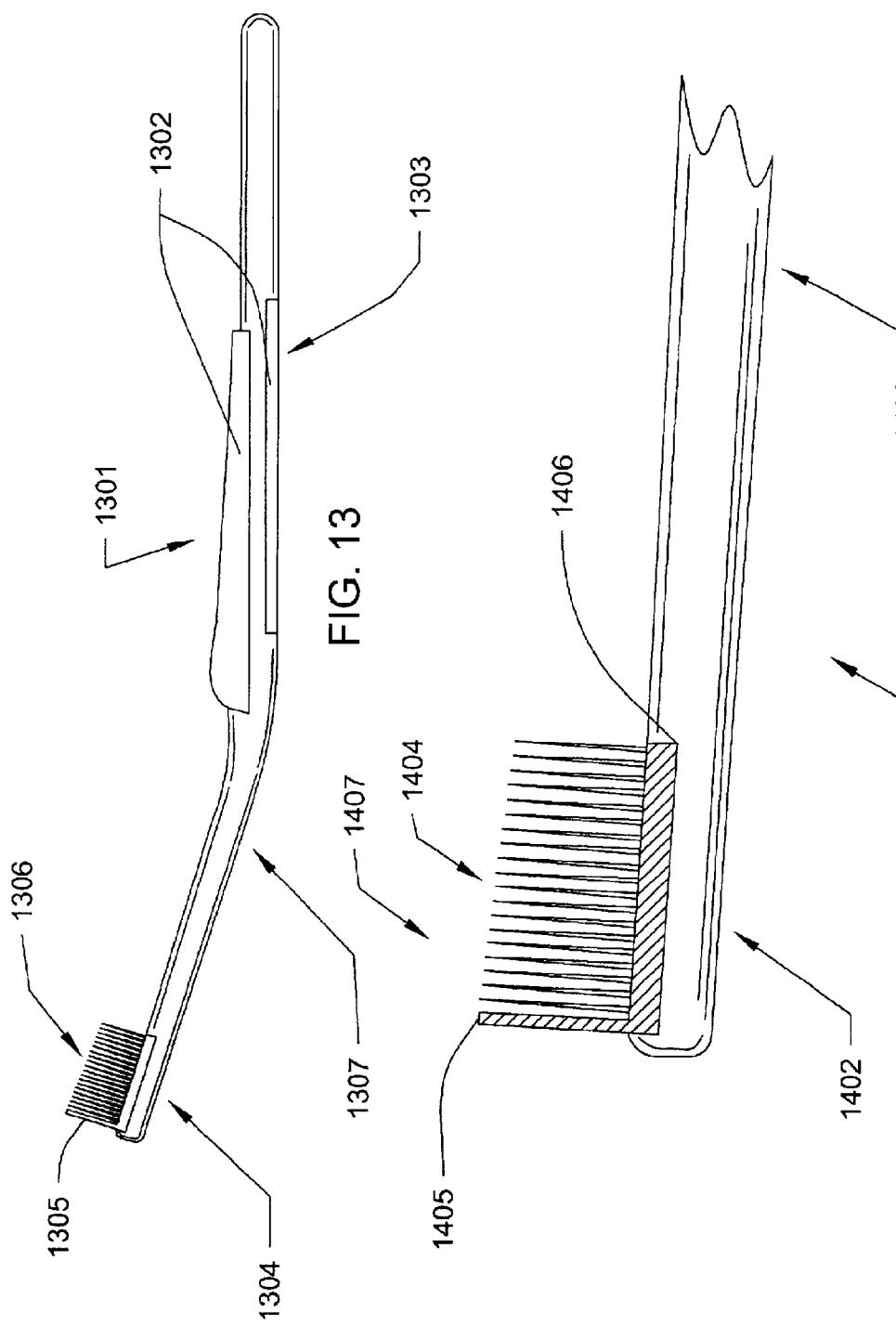

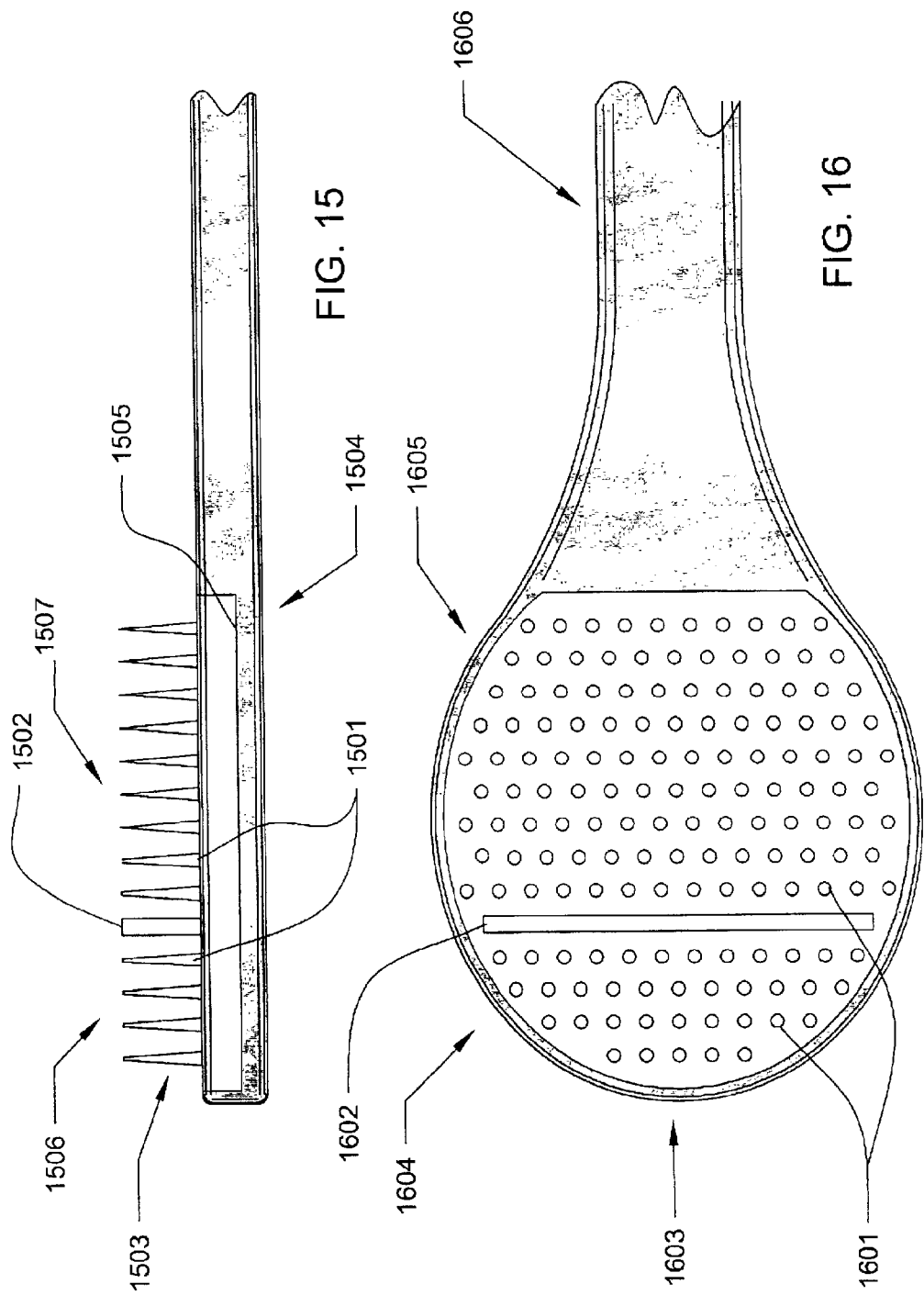

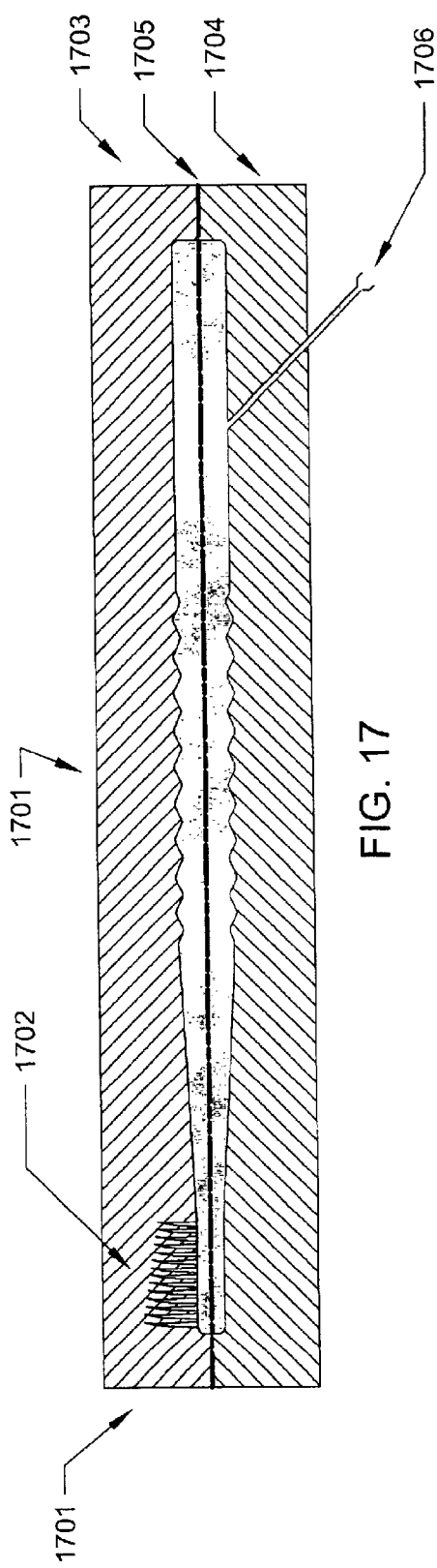
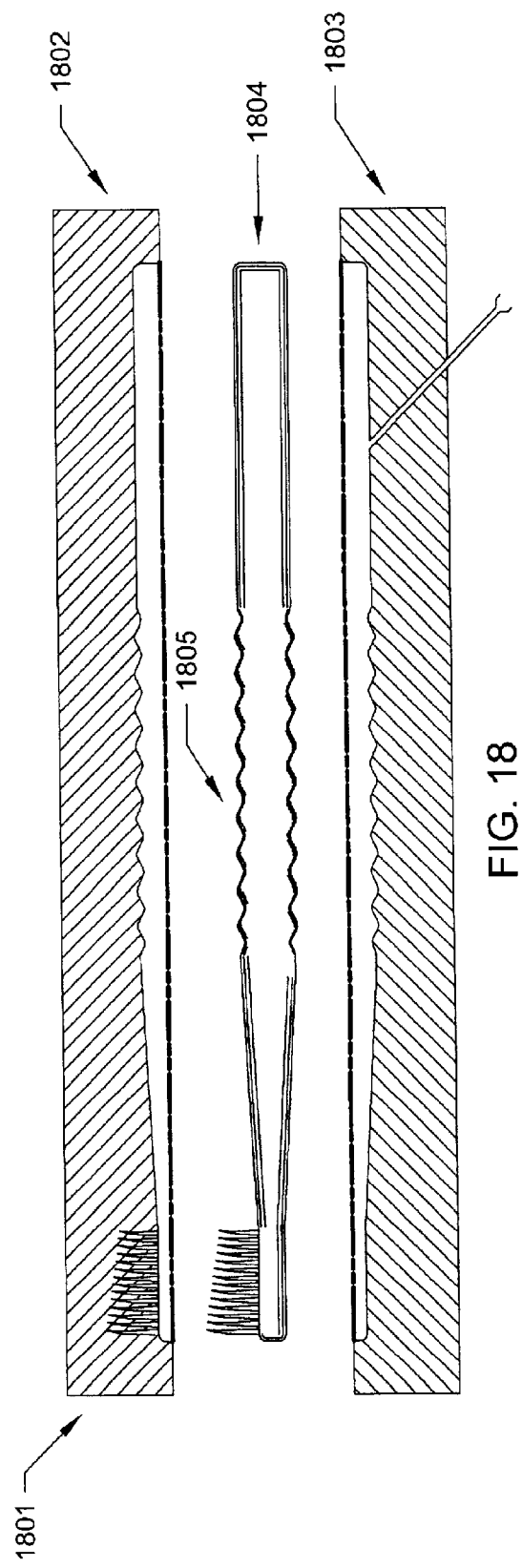
FIG. 17
FIG. 18

TONGUE CLEANING DEVICE

BACKGROUND OF THE INVENTION

This invention relates to the field of devices for cleaning the human tongue, and methods for making the same. In recent years, oral hygiene has become more important to the general public. The past misconception that bad breath (halitosis) is primarily caused by dirty teeth or stomach gases is now being corrected. It is now established that the primary cause of bad breath is due to bacteria that live on the top surface of the tongue. These bacteria produce odors and deposit waste material on the surface of the tongue. In order to control bad breath, bacteria and their waste materials must be removed.

The tongue surface contains many small openings where taste buds and salivary glands reside. These small openings can contain waste material which adversely affects their function. In severe cases the person may lose a significant amount of his or her sensation of taste. Such waste material may also impair the function of salivary glands, causing the mouth to feel dry. In addition, the surface of the tongue is physically uneven and the surface cells are sensitive to injury. Therefore, the removal of the bacteria and waste material may be performed by both a physical brushing as well as a tongue scraping, while respecting the sensitivity of the tongue.

SUMMARY OF THE INVENTION

Objects of the inventions include providing a device for cleaning the human tongue, and providing methods for making devices for cleaning the human tongue. Additional objects, features and advantages of the inventions will become apparent to persons of ordinary skill in the art upon reading this document in light of the appended drawings.

BRIEF DESCRIPTION OF THE DRAWINGS

FIG. 3 depicts a latitudinal front view of a tongue cleaning device.

FIG. 4 depicts a latitudinal side view of a tongue cleaning device.

FIG. 5 depicts an enlarged latitudinal side view of the tongue brush head and tongue scraper of FIG. 6 depicts an enlarged latitudinal side view of one tapered point bristle of the tongue cleaner of FIG. 5.

FIG. 7 depicts an enlarged latitudinal side view of one cut point bristle.

FIG. 8 depicts a latitudinal side view of a tongue scraper.

FIG. 9 depicts an enlarged latitudinal side view of three tongue scraper blades.

FIG. 10 depicts a longitudinal side view of three tongue scraper blades in a passive position.

FIG. 11 depicts a longitudinal side view of three tongue scraper blades in an active position.

FIG. 12 depicts a latitudinal front view of a tongue scraper head.

FIG. 13 depicts a latitudinal side view of a tongue cleaning device with an angled neck.

FIG. 14 depicts a latitudinal side view of the distal end of a tongue cleaning device.

FIG. 15 depicts a latitudinal side view of a head region of a tongue cleaning device.

FIG. 16 depicts a latitudinal front view of the distal end of a tongue cleaning device.

FIG. 17 depicts the molding stage of a tongue cleaning device one-step injection molding process.

FIG. 18 depicts the ejection stage of a tongue cleaning device injection molding process.

DETAILED DESCRIPTION

Figure 1:
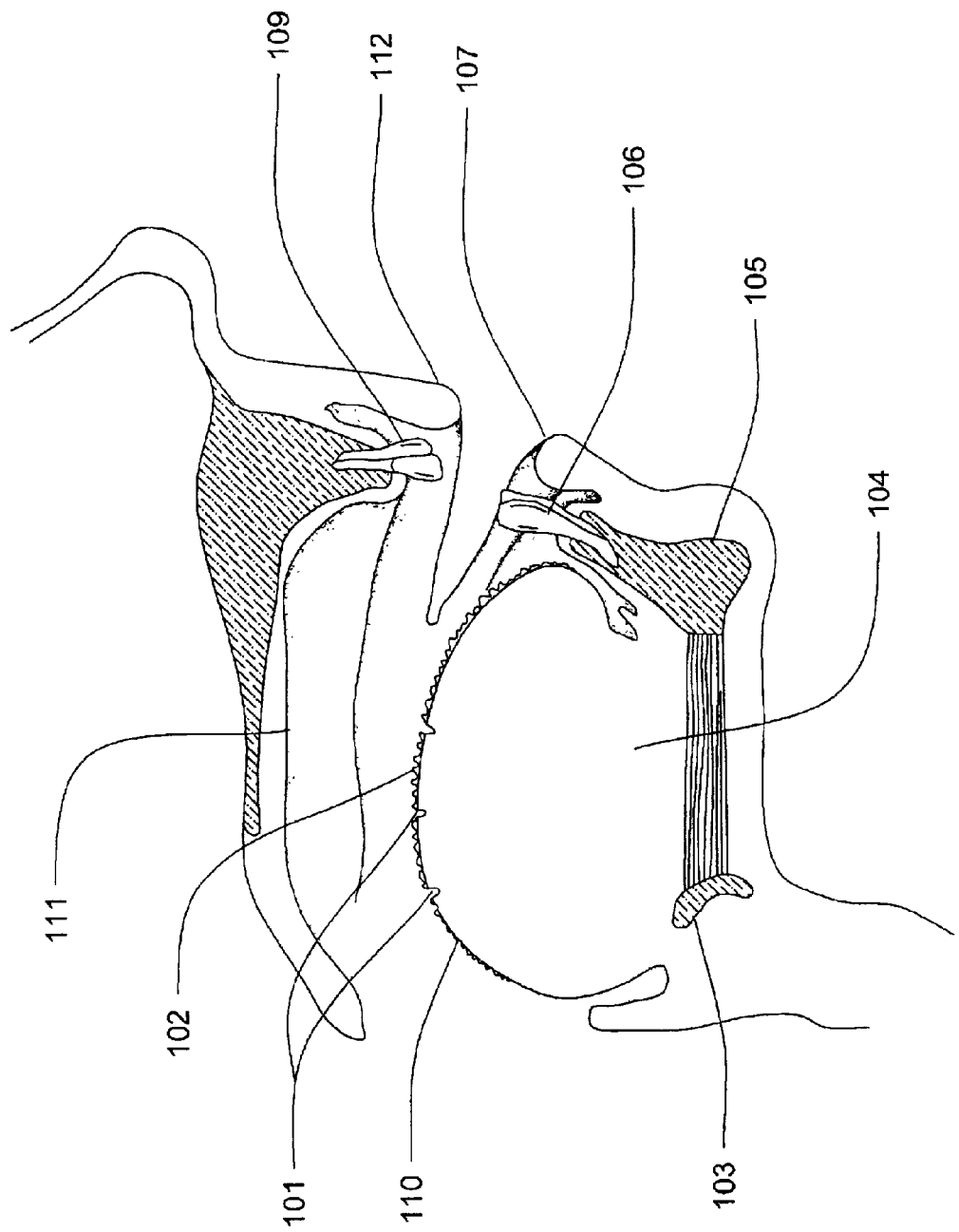
FIG. 1 depicts a longitudinal cross-section side view of the human tongue and surrounding anatomy.

Referring to FIG. 1, the human tongue 110 is substantially all muscle 104, and has a surface made up of taste buds 101 and papillae (also referred to as mucous membrane) 102. The hyphoid bone 103 is directly beneath the tongue 110, and the hard palate 111 is directly above the tongue 110. The jaw bone 105, lower teeth 106, lower lip 107, upper lip 112 and upper teeth 109 outline the human mouth orifice. This cross-sectional view illustrates in a minor degree the roughness and crevices of the human tongue which present a particularly difficult cleaning task.

Figure 2:
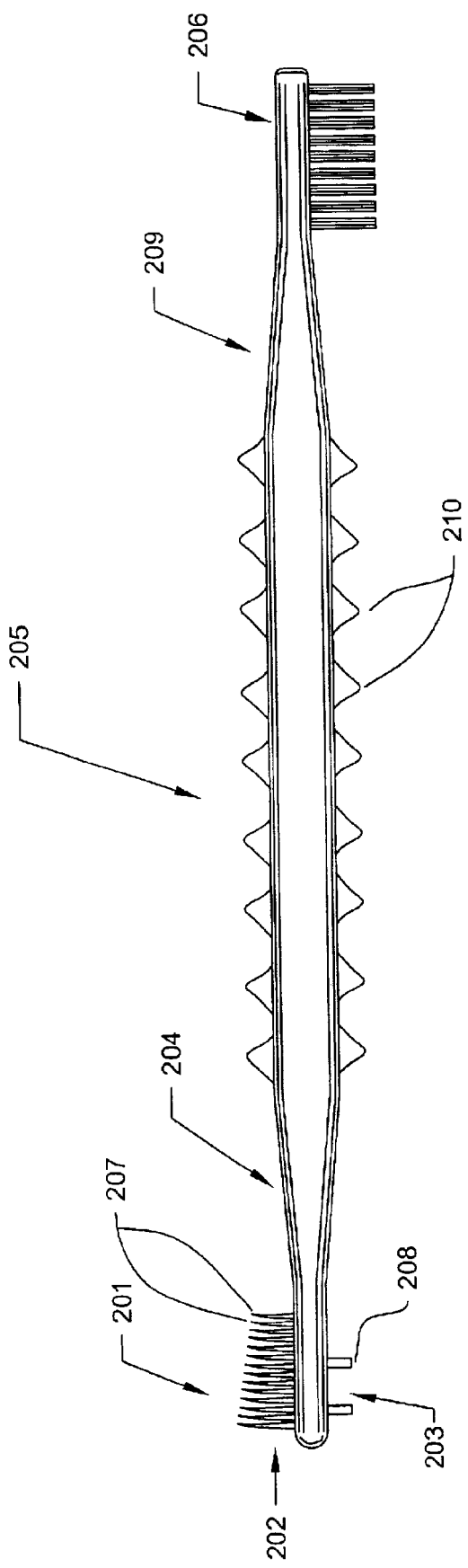
FIG. 2 depicts a longitudinal side view of a tongue cleaner and toothbrush combination device.

An embodiment of a tongue cleaning device of the invention is depicted in FIG. 2. The device depicted is a combination tongue brush/tongue scraper/toothbrush in order to present the user with maximum utility in a single article. The device has an elongated member that includes a head region 201 at the distal end, a neck 204, and a handle 205 at the proximal end, wherein said neck emanates from said handle. The head region 201 contains a tongue brush 202 on its first side and a tongue scraper 203 on its second and opposite side. This permits the user to brush his tongue, turn the device over, and use the scraper to scrape away material loosened by brushing. The tongue brush 202 includes a plurality of flexible bristles 207 that are tapered or cut to a point. The bristles are individually mounted, non-tufted bristles. The bristles may bend or arch slightly toward the handle if desired. The tongue scraper 203 includes one or more tongue scraper blades 208. The blades 208 may be as flexible or rigid as desired. A toothbrush 206 extends from the proximal end of the handle 205 via a second neck 209. The embodiment of FIG. 2 also has ridged finger grips 210 to enhance handling and manipulation of the tongue cleaning device. It can be seen from FIG. 2 that the bristles 207 emanate from a supporting base or bristle base.

FIG. 3 depicts a frontal view of a tongue cleaning device, showing only the tongue brush 301, head region 302, neck 303, handle 304, and bristles 305. The bristles are arranged in an arcuate swath across the head, in individually mounted non-tufted format. The bristles may be arranged in rows or other formations as desired. FIG. 4 shows a side view of a tongue cleaning device, wherein a tongue scraper 401 is on the opposite side of the tongue brush 402. This embodiment shows the individually mounted bristles 403 of the tongue cleaning device. The bristles 403 are curved at an angle toward the handle 404 and are each tapered to a point. The tongue scraper 401 has a squared off edge 405, but may include a sharp or rounded edge as desired.

FIG. 5 illustrates an enlarged view of the individually mounted bristles 501 of the tongue brush 502. The bristles 501 are curved at an angle toward the handle 503 and formed to taper to a point. The scraper 504 has a squared off edge 505. FIG. 6 illustrates the angle of curvature of each individual bristle 601. FIG. 7 illustrates an alternative bristle 701 that is cut or formed to have an angled point 702. It can be seen from FIGS. 3–5 that the bristles of the tongue cleaner emanate from a base or bristle base that is attached to the tongue cleaner neck.

FIG. 8 shows a side view of a tongue scraper 801. This embodiment shows three sets of primary 803 and secondary 802 flexible scraper blades. The pair of secondary scraper blades 802 are shorter in height than the single primary scraper blade 803 and are located on either side of it. They serve to provide the primary scraper blade 803 with lateral structural support and increase its effectiveness. In the event the primary blade does not collect all of the debris, a secondary blade may pick up the remainder.

FIG. 9 illustrates one set 901 of a pair of secondary scraper blades 902 and a single primary scraper blade 903 used to form a tongue scraper. FIG. 10 shows the primary 1003 and secondary blade 1002 positions for a passive tongue scraper 1001. FIG. 11 shows the primary 1103 and secondary blade 1102 active position of the tongue scraper 1101. In this particular embodiment, the secondary blades 1102 may provide structural support for the primary scraper blade 1103 and increased effectiveness of the tongue scraper. FIG. 12 is a frontal view of a tongue scraper 1202, wherein a single primary blade 1204 and pair of secondary blades 1203 are shown as a set 1201. Three such sets are provided to enhance scraping action.

FIG. 13 shows a tongue cleaning device 1301, wherein the neck 1307 is angled for ease in applying pressure to the tongue while cleaning. The neck 1307 can be angled from about 0 degrees to about 45 degrees or more with the longitudinal axis of the handle 1303 of the device 1301. The head region 1304 has both a tongue scraper 1305 and a tongue brush 1306 on the same side, wherein the tongue scraper 1305 is proximal to the tongue brush 1306. Finger grip strips 1302 extend along a portion of the handle 1303 for superior gripping.

FIG. 14 shows the components of a tongue cleaning device head region 1402 and neck 1403. An elongated member 1401 is molded from a rigid material. The tongue scraper 1405 and a tongue brush 1404 are of unitary construction and from a second less-rigid material. The tongue scraper 1405 is distal to the tongue brush 1404. The tongue scraper and tongue brush component 1407 are joined with the elongated member 1401 via mechanical grip and/or chemical affinity or bond at knit line 1406. It can be seen from FIGS. 13 and 14 that the bristles of the tongue cleaner emanate from a bristle base formed as a unitary member with the bristles themselves.

FIG. 15 illustrates an alternative embodiment wherein a tongue scraper 1502 is located between a first 1506 and second colony 1507 of bristles 1501. The bristles are depicted as being arranged in row and column format but could be arranged otherwise as desired. A few rows of bristles 1501 are located in the first colony 1506, on the distal side of the tongue scraper 1501. Several more rows of bristles 1501 are located in the second colony 1507, on the proximal side of the tongue scraper 1502. The elongate member 1504 is formed using a generally rigid material. The tongue scraper and tongue brush component 1503 may be of unitary construction or may be formed in separate manufacturing steps and joined together. The tongue scraper and tongue brush component 1503 will be formed of a more flexible material then the elongate member 1504. The tongue scraper and tongue brush components 1503 are attached to the elongate member 1504 via mechanical grip and/or chemical affinity or bond at knit line 1505. It can be seen from FIG. 15 that the bristles of the tongue cleaner emanate from a bristle base formed as a unitary member with the bristles themselves. The bristle base is joined with other components of the tongue cleaner.

FIG. 16 illustrates a frontal view of an embodiment of the invention, wherein a tongue scraper 1602 is located in between a first 1604 and second colony 1605 of bristles 1601, on the same side of the head region 1603. The user is able to control the amount of tongue brush and/or scraper contact by manipulating the angle of the handle 1606 as it is rotated about the longitudinal access of the scraper blade 1602 which acts as a fulcrum.

The above material describes generally structures of some embodiments of the inventions. Below, a description is provided of equipment and apparatuses useful for injection molding various tongue cleaners of the invention.

The general steps involved in injection molding a tongue cleaner of the invention include: (a) obtain or create a mold having an interior cavity reflective of the structure of tongue cleaner which is desired to be manufactured, (b) obtain a quantity of plastic or other suitable material for forming the tongue cleaner, (c) melt the plastic or other material until it is flowable, (d) force the flowable plastic or other material into the mold cavity, (e) permit the plastic or other material to cool and solidify in the cavity, (f) open the mold, and (g) remove the molded tongue cleaner. These steps will be elucidated in the text below in reference to the corresponding figures.

FIG. 17 shows a mold 1701 for injection molding a tongue cleaning device. This mold is used for a one-step unitary construction of a tongue cleaning device. This embodiment illustrates formation of only a tongue brush 1702, although a combination tongue brush and/or tongue scraper with or without a toothbrush could also be formed as desired. The mold 1701 includes a first mold half 1703 and a second mold half 1704. These two mold halves are separated by a center line 1705. When the mold 1701 is fitted together as shown in FIG. 17, molding material is forced through the portal 1706 to form the tongue brush 1702. The formed tongue brush 1702 is then allowed to cool and solidify.

FIG. 18 shows an open mold 1801 following completion of injection molding from the previous figure. The top 1802 and bottom 1803 mold halves were separated along the center line 1804 to yield a finished product tongue cleaner device 1805 which is of unitary construction.

Figure 19:
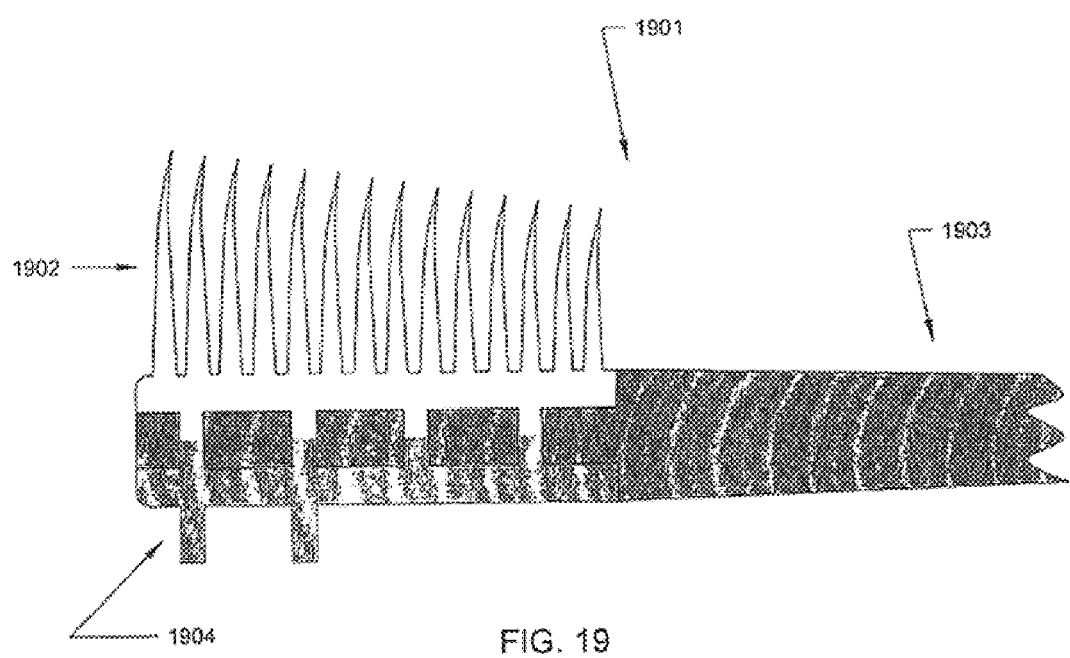
FIG. 19 depicts tongue cleaner componentry formed by a multiple step injection molding process.

FIG. 19 illustrates a tongue cleaning device 1901 formed via a multiple-step injection molding process. This device 1901 is formed of multiple components each of which is individually molded. First, the tongue brush 1902 was molded from a first material. Then a second different material is used to form a tongue scraper 1904. A third more rigid material is used to form an elongated member 1903. These separate molding steps will typically be performed in separate molds, moving the partially-molded component from mold to mold until completion. The separate components are affixed to each other mechanically, by adhesive such as glue or epoxy, by welding, or by affinity or chemical bond during injection molding. It can be seen from FIG. 19 that the bristles of the tongue cleaner emanate from a bristle base formed as a unitary member with the bristles themselves. The bristle base is joined with other components of the tongue cleaner.

Figure 20:
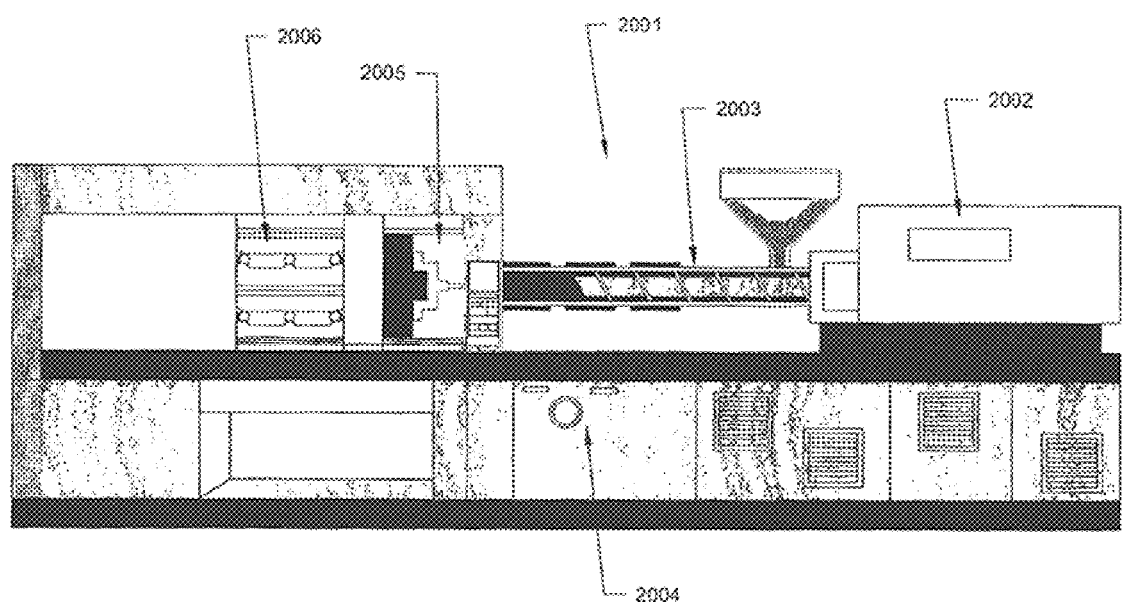
FIG. 20 depicts a latitudinal side view of an injection molding machine.

FIG. 20 illustrates an injection molding machine 2001 which may be used to make tongue cleaners of the invention. The injection molding machine includes five systems. These systems include: the hydraulic system 2002, the injection system 2003, the control system 2004, the mold system 2005, and the clamping system 2006. The hydraulic system 2002 provides the power to run the injection system 2003, the mold system 2005, and the clamping system 2006. The injection system 2003 confines, melts and transports the plastic as it progresses through various stages in the machine 2001. The control system 2004 provides consistency and repeatability in machine operation. The mold system 2005 forms the molten plastic into a tongue cleaner. The clamping system 2006 opens and closes the mold, and supports and carries constituent parts of the mold.

Figure 21:
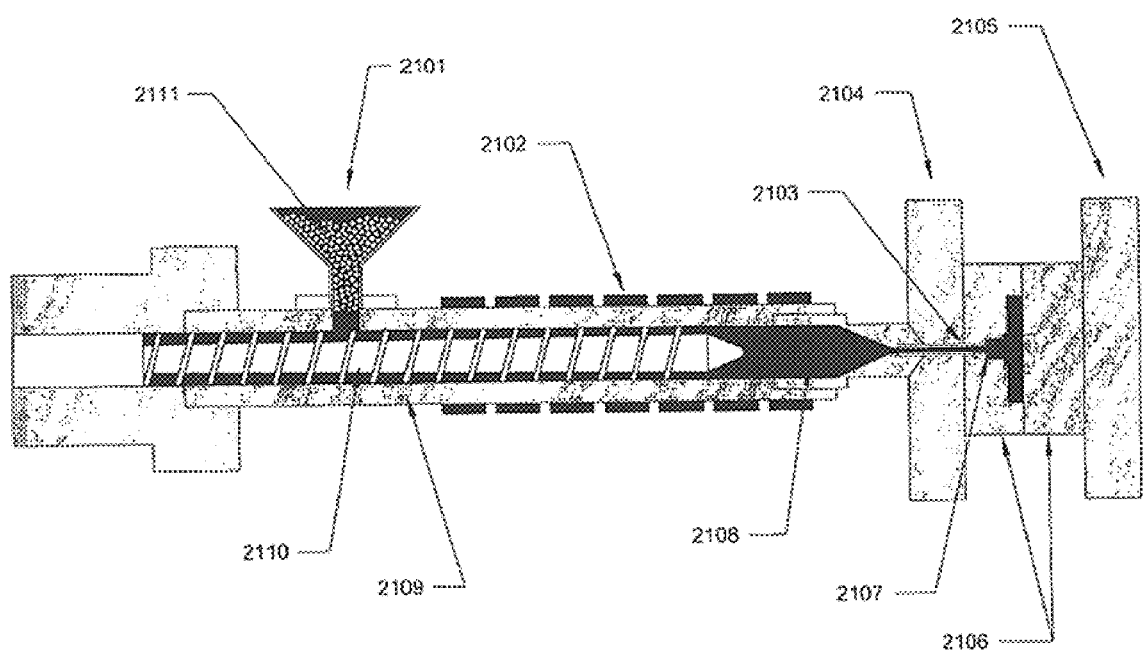
FIG. 21 depicts a latitudinal side view of the injection system of an injection molding machine.

FIG. 21 illustrates the injection system of an injection molding machine useful when making injection molded tongue cleaners of the invention. Raw materials 2111, generally in the form of small pellets, are put into the hopper 2101. A barrel 2109 receives raw material 2111 from the hopper 2101 and supports a reciprocating plasticizing screw 2110. The barrel 2109 is heated by electric heater bands 2102, which melts the raw material that is located within the barrel 2109, permitting it to be plasticized by the turning screw 2110. The injection chamber 2108 delivers the material to the nozzle 2103. The nozzle 2103 connects the barrel 2109 to the sprue bushing 2107 of the mold 2106 and forms a seal between the barrel 2109 and the mold 2106. Molten raw material from the barrel 2109 is forced by the screw 2110 through the nozzle 2103 into the sprue bushing 2107 and into the mold 2106 where it can assume the shape of the interior cavity of the mold. A movable platen 2105 detaches from a stationary platen 2104 to separate the mold halves and eject the molded tongue cleaner.

A discussion is provided below of some features and characteristics of some embodiments of the tongue cleaner inventions. This discussion should not be considered limiting as to the scope of the inventions. A tongue cleaning device may consist of a head region, neck and handle. The head region is distally connected to the handle via the neck. The neck may be the narrowest portion of the tongue cleaning device. The handle is at the proximal end of the tongue cleaning device. The neck and/or handle may be angled to facilitate pressure control of the device on the tongue.

One embodiment of the inventions consists of a tongue brush attached to the head region, where the tongue brush is approximately 32 mm long by 16–25 mm wide and 4 mm thick. The head and tongue brush are attached to a handle that is approximately 170 mm long, 12 mm wide and 5 mm thick. The handle can have finger grips formed of the same or a different material. The finger grips can be ridges or long strips of material. The grips are designed to facilitate handling and manipulating the tongue cleaning device.

The tongue brush includes a bristle base, which is approximately 4 mm thick. A plurality of individually mounted non-tufted bristles emanates from the bristle base. The individual bristles can be formed of the same material as the base or from another material as desired. Each bristle is individually mounted on the base, formed of solid material and tapered to a point. The bristles may be of different lengths such that those at the distal end of the brush are longer (approximately 10 mm in length) and those toward the neck are shorter (approximately 5 mm in length). The bristles may be individually cut at an angle to form a point. In addition, all of the bristles are curved toward the handle of the brush.

The curvature of the bristle, along with the different bristle lengths, allows for the bristles to touch the tongue while in use. The points of the bristles are also small enough to enter into the small indentations and crevices of the tongue surface and loosen and remove the bacteria and waste material. The bristles are soft and will not damage the surface cells of the tongue. In addition, the user can regulate bristle pressure by pivoting the tongue cleaning device about its longitudinal axis.

The tongue scraper may include one or more blades that can also be formed of the same material or a different material as the tongue brush. The tongue scraper can be on the same (first) or opposite (second) side of the tongue brush. The scraper can be made up of single or multiple blades. The scraper blades emanate from the bristle base. In addition, the blades can be located above, below or in between the bristles. In one embodiment, the blade(s) are approximately 3 mm long and about 0.5 mm thick. The edge of the blade is flat (or square) and flexible. As the scraper is pulled across the surface of the tongue the loosened bacteria and waste material is gently carried out of the mouth. The forward edge of the blade is the "active" edge of the scraper.

In an alternative embodiment the tongue scraper is comprised of sets of one primary blade and two secondary blades. One secondary blade is located on either side of the primary blade. Both blades function much like a window scraper that removes water from a glass window. The secondary blade provides additional strength and effectiveness. This type of scraper is efficient and gentle to the surface of the tongue. Again, the user can regulate the scraper blade(s) pressure by pivoting the tongue brush about the longitudinal axis of the scraper blade.

The tongue brush and the tongue scraper can be formed together as one instrument or they can be built and used separately. In addition, a toothbrush may be incorporated on the proximal end of the handle via a second neck to form a tooth and tongue cleaning device. Alternatively, the toothbrush may be joined to only a tongue scraper or a tongue brush. The toothbrush can be joined to the tongue cleaning device via welding, mechanical fixation or being formed during the injection molding process.

In some embodiments of the inventions, the tongue cleaning device may be made by injection molding. The first step is to obtain or create a suitable mold. The mold can be formed of machined metal such as aluminum or steel to have an interior cavity reflecting the shape of the tongue cleaner to be produced. The mold is then used in an injection molding machine which forces molten raw material, such as plastic, into the mold cavity to form the tongue cleaner. The injection molding process may be a single step or series of steps, depending on the number of materials used. Possible materials for making the invention and components thereof include: polypropylene, polyethylene, polystyrene, thermoplastic rubber, resin, silicon rubber, natural rubber, plastic and other materials.

In one embodiment of the invention, the tongue cleaner may be formed by a one-step injection molding process wherein a single material, such as polypropylene, is used to form the entire tongue cleaning device, such that a single mold is used to form all portions of the tongue brush in a single step. The mold would yield the entire tongue cleaning device of unitary construction upon being opened.

An alternative embodiment is to use two or more molds wherein plastics, for example, of differing degrees of rigidity would be molded separately to form distinct components of a tongue cleaning device. These separately molded portions can be fitted together via a mechanical grip and/or chemical affinity or bond. One embodiment of a multiple step injection molding process is to have three molds, wherein the first mold forms the elongated member, the second mold forms the tongue brush and tongue scraper, and a third mold forms finger grips.

While the present invention has been described and illustrated in conjunction with a number of specific embodiments, those skilled in the art will appreciate that variations and modifications may be made without departing from the principles of the invention as herein illustrated, described, and claimed.

The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A tongue cleaner comprising:
   a handle configured and adapted to be grasped by a human hand, the handle having a longitudinal axis,
   a neck emanating from said handle,
   a head region located distal to said neck,
   a tongue brush located in said head region, said tongue brush including:
      a bristle base configured to be a substantially rigid platform that will support tongue brush bristles in use, said bristle base having a proximal end adjacent said neck, a distal end, a top and a bottom, and
      a plurality of bristles emanating from said bristle base top, each of said bristles having a proximal end adjacent said bristle base and a distal end, at least some of said bristles being tapered from their proximal end to their distal end to present a pointed bristle appearance,
      at least some of said bristles being of differing heights, said bristles being arranged generally in order of descending height from said bristle base distal end to said bristle base proximal end,
      at least some of said bristles having a curvature that causes them to curve toward said neck,
      said bristles being flexible to accommodate brushing of a human tongue without causing injury to the tongue,
      said bristles and said bristle base being formed as a single unitary component from the same material via an injection molding process,
      said bristles emanating from said bristle base top in an individually-mounted and free-standing non-tufted configuration, and
   a tongue scraper emanating from said bristle base top, said tongue scraper including:
      at least a first tongue scraper blade, said first tongue scraper blade having sufficient flexibility to be useful in removing undesirable material from a human tongue by a scraping action.

2. A device as recited in claim 1 wherein a second tongue scraper blade emanates from said bristle base bottom.

3. A device as recited in claim 1 wherein said handle, neck, bristle base, bristles and tongue scraper are formed as a single unitary component formed from a single material by an injection molding process.

4. A device as recited in claim 1 wherein at least a portion of the tongue cleaner includes a material selected from the group consisting of polypropylene, polyethylene, polystyrene, thermoplastic rubber, resin, silicon rubber, natural rubber and plastic.

5. A device as recited in claim 1 wherein said neck is oriented at an angle of less than 180 degrees with said handle longitudinal axis.

6. A device as recited in claim 1
   further comprising a plurality of tongue scraper blades arranged in rows in the head region of the device;
   wherein each of said tongue scraper blades has a longitudinal axis; and
   wherein each of said tongue scraper blades is oriented with respect to said handle so that said tongue scraper blade longitudinal axis is generally orthogonal to said handle longitudinal axis.

7. A device as recited in claim 1 further comprising finger grips located on said handle to enhance secure gripping of the handle.

8. A tongue cleaner comprising:
   a handle configured and adapted to be grasped by a human hand, the handle having a longitudinal axis,
   a neck emanating from said handle,
   a head region located distal to said neck,
   a tongue brush located in said head region, said tongue brush including:
      a bristle base configured to be a substantially rigid platform that will support tongue brush bristles in use, said bristle base having a proximal end adjacent said neck, a distal end, a top and a bottom;
      a plurality of bristles emanating from said bristle base top, each of said bristles having a proximal end adjacent said bristle base and a distal end, at least some of said bristles being tapered from their proximal end to their distal end to present a pointed bristle appearance,
      at least some of said bristles being of differing heights, said bristles being arranged generally in order of descending height from paid bristle base distal end to said bristle base proximal end,
      at least some of said bristles having a curvature that causes them to curve toward said neck,
      said bristles being flexible to accommodate brushing of a human tongue without causing injury to the tongue,
      said bristles and said bristle base being formed as a single unitary component from the same material via an injection molding process,
      said bristles emanating from said bristle base top in an individually-mounted and free-standing non-tufted configuration, and
   a tongue scraper located in said head region, said tongue scraper including:
      at least one tongue scraper blade, said tongue scraper blade having sufficient flexibility to be useful in removing undesirable material from a human tongue by a scraping action, said tongue scraper blade emanating from said bristle base top adjacent said bristles.

9. A tongue cleaner comprising:
   a handle configured and adapted to be grasped by a human hand, the handle having a longitudinal axis,
   a neck emanating from said handle,
   a head region located distal to said neck,
   a tongue brush located in said head region, said tongue brush including:
      a bristle base configured to be a substantially rigid platform that will support tongue brush bristles in use, said bristle base having a proximal end adjacent said neck and a distal end, and a plurality of bristles emanating from said bristle base, each of said bristles having a proximal end adjacent said bristle base and a distal end, at least some of said bristles being tapered from their proximal end to their distal end to present a pointed bristle appearance, at least some of said bristles being of differing heights, said bristles being arranged generally in order of descending height from said bristle base distal end to said bristle base proximal end, at least some of said bristles having a curvature that causes them to curve toward said neck, said bristles forming a first colony at said bristle base distal end and a second colony at said bristle base proximal end, said bristles being flexible to accommodate brushing of a human tongue without causing injury to the tongue, said bristles and said bristle base being formed as a single unitary component from the same material via an injection molding process, said bristles emanating from said bristle base in an individually-mounted and free-standing non-tufted configuration, and a tongue scraper located in said head region, said tongue scraper including:

at least one tongue scraper blade, said tongue scraper blade having sufficient flexibility to be useful in removing undesirable material from a human tongue by a scraping action, said tongue scraper blade emanating from a location between said first and second bristle colony.

10. A tongue cleaner comprising:

a handle configured and adapted to be grasped by a human hand, the handle having a longitudinal axis, a neck emanating from said handle, a head region located distal to said neck, a tongue brush located in said head region, said tongue brush including:

a bristle base configured to be a substantially rigid platform that will support tongue brush bristles in use, said bristle base having a proximal end adjacent said neck and a distal end, and a plurality of bristles emanating from said bristle base, each of said bristles having a proximal end adjacent said bristle base and a distal end, at least some of said bristles being tapered from their proximal end to their distal end to present a pointed bristle appearance, at least some of said bristles being of differing heights, said bristles being arranged generally in order of descending height from said bristle base distal end to said bristle base proximal end, at least some of said bristles having a curvature that causes them to curve toward said neck, said bristles being flexible to accommodate brushing of a human tongue without causing injury to the tongue, said bristles and said bristle base being formed as a single unitary component from the same material via an injection molding process, said bristles emanating from said bristle base in an individually-mounted and free-standing non-tufted configuration, a tongue scraper located in said head region, said tongue scraper including:

at least one tongue scraper blade, said tongue scraper blade having sufficient flexibility to be useful in removing undesirable material from a human tongue by a scraping action, said tongue scraper blade emanating from said bristle base, wherein said bristle base and bristles are formed from a first material by a first injection molding process, and the remainder of the tongue cleaner is formed from a second material by a second injection molding process; and wherein said first material and said second material differ from each other.

11. A tongue cleaner comprising:

a handle configured and adapted to be grasped by a human hand, the handle having a longitudinal axis, a neck emanating from said handle, a head region located distal to said neck, a tongue brush located in said head region, wherein said tongue brush is formed from a first material by a first injection molding process, said tongue brush including:

a bristle base configured to be a substantially rigid platform that will support tongue brush bristles in use, said bristle base having a proximal end adjacent said neck and a distal end, and a plurality of bristles emanating from said bristle base, each of said bristles having a proximal end adjacent said bristle base and a distal end, at least some of said bristles being tapered from their proximal end to their distal end to present a pointed bristle appearance, at least some of said bristles being of differing heights, said bristles being arranged generally in order of descending height from said bristle base distal end to said bristle base proximal end, at least some of said bristles having a curvature that causes them to curve toward said neck, said bristles being flexible to accommodate brushing of a human tongue without causing injury to the tongue, said bristles and said bristle base being formed as a single unitary component from the same material via an injection molding process, said bristles emanating from said bristle base in an individually-mounted and free-standing non-tufted configuration, a tongue scraper located in said head region, wherein said tongue scraper is formed from a second material by a second injection molding process, said tongue scraper including:

at least one tongue scraper blade, said tongue scraper blade having sufficient flexibility to be useful in removing undesirable material from a human tongue by a scraping action, said tongue scraper blade emanating from said bristle base, wherein said handle and neck are formed by a from a third material by a third injection molding process; and wherein each of said first material, said second material and said third material are different from each other.

12. A tongue cleaner comprising:

a handle configured and adapted to be grasped by a human hand, the handle having a longitudinal axis, a neck emanating from said handle, wherein said handle and neck are formed from a first material by a first injection molding process, a head region located distal to said neck, a tongue brush located in said head region, said tongue brush including:
- a bristle base configured to be a substantially rigid platform that will support tongue brush bristles in use, said bristle base having a proximal end adjacent said neck and a distal end,
- a plurality of bristles emanating from said bristle base, each of said bristles having a proximal end adjacent said bristle base and a distal end, at least some of said bristles being tapered from their proximal end to their distal end to presented a pointed bristle appearance,
- said bristles being flexible to accommodate brushing of a human tongue without causing injury to the tongue,
- said bristles and said bristle base being formed as a single unitary component from a second material via a second injection molding process,
- said bristles emanating from said bristle base in an individually-mounted and free-standing non-tufted configuration, and
- a tongue scraper located in said head region, wherein said tongue scraper is formed from a third material by a third injection molding process,
- wherein each of said first material, said second material and said third material are different from each other.

13. A device as recited in claim 12 wherein said bristles are arranged on said bristle base in a colony formation.

14. A device as recited in claim 12 wherein said bristles are arranged on said bristle base in a row formation.

15. A device as recited in claim 12 wherein at least a portion of the tongue cleaner includes a material selected from the group consisting of polypropylene, polyethylene, polystyrene, thermoplastic rubber, resin, silicon rubber, natural rubber and plastic.

16. A device as recited in claim 12 wherein said neck is oriented at an angle of less than 180 degrees with said handle longitudinal axis.

17. A device as recited in claim 12 further comprising finger grips located on said handle to enhance secure gripping of the handle by a user of the tongue cleaner.

18. A device as recited in claim 12 wherein at least some of said bristles are of a different length than other of said bristles.

19. A device as recited in claim 12 wherein said bristles terminate in a common plane.

20. A device as recited in claim 12 wherein at least some of said bristles are angled or curved with respect to said handle longitudinal axis.

21. A device as recited in claim 12 wherein at least some of said bristles are of a length greater than about 5 mm and less than about 10 mm.

22. A device as recited in claim 12 wherein at least some of said bristles have a base that is not more than about 1 mm in diameter.

23. A device as recited in claim 12 wherein said bristle base has a toy and a bottom, and said tongue scraper blade emanates from said bristle base top, said tongue scraper blade having sufficient flexibility to be useful in removing undesirable material from a human tongue by a scraping action.

24. A device as recited in claim 12 further comprising a plurality of tongue scraper blades in said head region.

25. A device as recited in claim 24 wherein said tongue scraper blades include at least one primary tongue scraper blade and at least one secondary tongue scraper blade, said secondary tongue scraper blades serving to mechanically reinforce said primary tongue scraper blade.

* * * * *